United States Patent [19]

Atsumi et al.

[11] 4,318,925
[45] Mar. 9, 1982

[54] 4-HOMOISOTWISTANE DERIVATIVES

[75] Inventors: Toshio Atsumi, Ashiya; Yoshiaki Takebayashi, Toyonaka; Masaru Fukui, Takarazuka; Hisao Yamamoto, Kobe, all of Japan

[73] Assignees: Sumitomo Chemical Co., Ltd., Osaka; Kao Soap Co., Ltd., Tokyo, both of Japan

[21] Appl. No.: 132,135

[22] Filed: Mar. 20, 1980

Related U.S. Application Data

[63] Continuation of Ser. No. 917,799, Jun. 22, 1978, abandoned.

[30] Foreign Application Priority Data

Jul. 4, 1977 [JP] Japan .................. 52-80124

[51] Int. Cl.³ .......................... C07C 103/37
[52] U.S. Cl. .................. 424/324; 564/175; 564/192; 564/193
[58] Field of Search .............. 564/175, 192, 193; 424/324

[56] References Cited

U.S. PATENT DOCUMENTS 3,705,194 12/1972 Scherm et al. .............. 564/193

FOREIGN PATENT DOCUMENTS 2555455 10/1975 Fed. Rep. of Germany.
1469069 12/1974 United Kingdom.
1508403 6/1975 United Kingdom.

OTHER PUBLICATIONS

Aigami et al. J. Med. Chem., 1976 (19) pp. 536–546.
Bognar et al. Chem. Abstracts, 81 (1974) #37330f.
May et al. Arneim-Forsch, 23(5) 1973, pp. 718–721.

*Primary Examiner*—Arthur P. Demers
*Attorney, Agent, or Firm*—Stevens, Davis, Miller & Mosher

[57] ABSTRACT

A new class of 4-homoisotwistane derivatives of the formula,

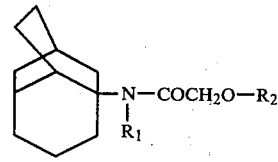

wherein $R_1$ is a hydrogen atom or a $C_1-C_3$ alkyl group, and $R_2$ is an alkyl group, a phenyl group which may be either unsubstituted or substituted with a $C_1-C_3$ alkyl, $C_1-C_3$ alkoxy, nitro group or a halogen atom (hereinafter referred to as "an optionally substituted phenyl group"), a group of the formula, —A—OH in which A is a $C_1-C_3$ alkylene group; a group of the formula, —A—B in which A is as defined as above and B is a halogen atom, or a group of the formula,

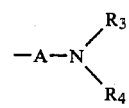

in which A is as defined above and $R_3$ and $R_4$ are independently a hydrogen atom or a $C_1-C_3$ alkyl group or $R_3$ and $R_4$ may, when taken together with the adjacent nitrogen atom to which $R_3$ and $R_4$ are linked, form pyrrolidine, piperidine, morpholine, phthalimide or piperazine, which have been found to possess potent antiviral activity, are prepared, for example by reacting a compound of the formula,

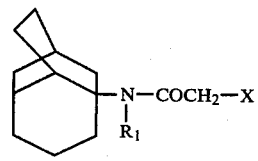

wherein $R_1$ is as defined above and X is halogen, with a compound of the formula, $R_5$ OY wherein $R_5$ has the same meanings as $R_2$ with the exception of the group of the formula —A—B wherein A and B are as defined above and Y is alkali metal.

6 Claims, No Drawings

4-HOMOISOTWISTANE DERIVATIVES

This is a continuation of application Ser. No. 917,799 filed June 22, 1978, now abandoned.

The present invention relates to 4-homoisotwistane derivatives and preparation thereof.

More particularly, the invention pertains to 4-homoisotwistane derivatives and non-toxic, pharmaceutically acceptable salts thereof, which are useful as antiviral agents, particularly for the treatment or prevention of infections caused by herpes or influenza viruses, and antiviral compositions containing them, and to preparation and use thereof.

There have been reported that 3-amino-4-homoisotwistane hydrochloride and some of its derivative have antiviral activity against Newcastle diseases virus [Koji Aigami et al., J. of Medicinal Chemistry, Vol. 19, 536 (1976)]. It is also known that 1-adamantanamine and some of its derivatives show antiviral against influenza viruses [British Pat. No. 1,063,366; SCIENCE, Vol. 144, 862, (1964)].

In view of the fact that hitherto known cage-molecular hydrocarbons generally have a relatively narrow antiviral spectrum and are weak in antiviral activity, we have carried out an extensive study seeking new derivatives having potent antiviral activity with a wide antiviral spectrum, and now found that 4-homoisotwistane derivatives of the formula [I] as hereinafter defined and non-toxic, pharmaceutically acceptable salts thereof have strong antiviral activity against both RNA and DNA viruses and low toxicity.

They have also been proved to have no serious side effects such as effects on central nervous system.

Thus, the compounds of the present invention are useful as antiviral agents having potent antiviral activity with a wide antiviral spectrum.

4-Homoisotwistane derivatives of the present invention is represented by the formula,

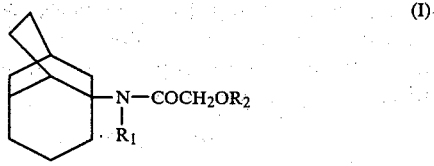
(I)

wherein $R_1$ is a hydrogen atom or a $C_1$–$C_3$ alkyl group, and $R_2$ is an alkyl group, a phenyl group which may be either unsubstituted or substituted with a $C_1$–$C_3$ alkyl, $C_1$–$C_3$ alkoxy, nitro group or a halogen atom (hereinafter referred to as "an optionally substituted phenyl group"); a group of the formula —A—OH in which A is a $C_1$–$C_3$ alkylene group; a group of the formula, —A—B in which A is as defind as above and B is a halogen atom; or a group of the formula,

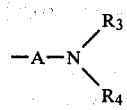

in which A is as defined above and $R_3$ and $R_4$ are independently a hydrogen atom or a $C_1$–$C_3$ alkyl group or $R_3$ and $R_4$ may, when taken together with the adjacent nitrogen atom to which $R_3$ and $R_4$ are linked, form pyrrolidine, piperidine, morpholine phthalimide or piperazine.

As used herein, the term, "$C_1$–$C_3$ alkyl" means a straight or branched alkyl having 1 to 3 carbon atoms (e.g. methyl, ethyl, n-propyl, or isopropyl). The term, "alkyl" means a straight or branched alkyl having one to eleven carbon atoms (e.g. methyl, ethyl, n-propyl, isopropyl, n-butyl, isobutyl, pentyl, hexyl, octyl, decyl or undecyl).

The term, "$C_1$–$C_3$ alkoxy" means a straight or branched alkoxy having 1 to 3 carbon atoms (e.g. methoxy, ethoxy, propoxy, isopropoxy).

The term, "halogen" includes fluorine, bromine and chlorine.

The term, "$C_1$–$C_3$ alkylene" means a alkylene having 1 to 3 carbon atoms and preferably includes methylene, ethylene and propylene.

In the present invention, 4-homoisotwistane derivatives of the formula (I) as above can be prepared by the following methods:

Method A

The 4-homoisotwistane derivatives of the formula,

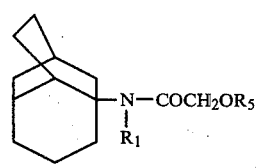
(I-a)

wherein $R_1$ is as defined above and $R_5$ has the same meanings as $R_2$ with the exception of the group of the formula —A—B wherein A and B are as defined above, can be prepared by reacting a compound of the formula,

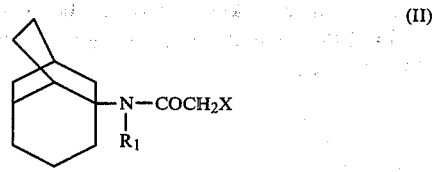
(II)

wherein $R_1$ is as defined above and X is a halogen atom, with a compound of the formula

$R_5OY$ (III)

wherein $R_5$ is as defined above and Y is an alkali metal.

The reaction can be carried out in an inert organic solvent under heating (preferably at a temperature from 80° C. to 150° C.).

Examples of the solvent to be used in this reaction are toluene, xylene and benzene.

The compound of the formula (III) can be prepared by reacting an alkali metal with an excess amount of a compound of the formula, $R_5OH$, wherein $R_5$ is as defined above, in a conventional manner, and may be used without isolation. Preferred example of alkali metal to be used in this process is sodium.

The compound of the formula (II) can be prepared by reacting a compound of the formula,

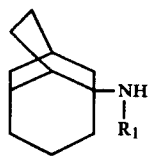

(IV)

wherein $R_1$ is as defined above, with a compound of the formula,

X—CH$_2$CO—X  (V)

wherein X is as defined above, in an inert organic solvent (e.g. benzene, toluene, xylene, or n-hexane) at a temperature from 0° C. to 150° C.

Preferred examples of the compound of the formula (V) are chloroacetylchloride or bromoacetylbromide.

It is preferable to use a half equivalent amount of the compound of the formula (V) to the compound of the formula (IV).

Method B

The 4-homoisotwistane derivatives of the formula,

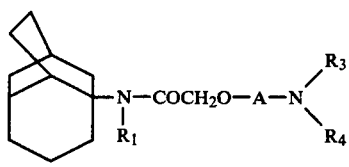

(I-b)

wherein $R_1$, A, $R_3$ and $R_4$ are as defined above, can be prepared by (1) reacting a compound of the formula,

YO—A—OH  (VI)

wherein Y and A are as defined above, with a compound of the formula (II) as above to give a compound of the formula,

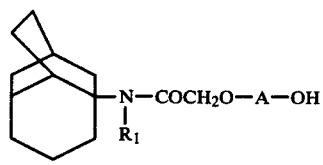

(VII)

wherein $R_1$ and A are as defined above, (2) reacting a compound of the formula (VII) with a halogenating agent to give a compound of the formula,

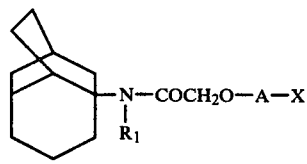

(VIII)

wherein $R_1$, A and X are as defined above, and (3) reacting a compound of the formula (VIII) with a compound of the formula,

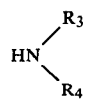

(IX)

wherein $R_3$ and $R_4$ are as defined above.

The first step of this process can be carried out by heating a compound of the formula (II) and a compound of the formula (VI) at a temperature from 100° C. to 200° C., preferably about 150° C.

The compound of the formula (VI) can be prepared by reacting alkali metal, preferably sodium, with an excess amount of a compound of the formula, HO—A—OH, wherein is as defined above, in a conventional manner and may be used without isolation.

The second step can be carried out by reacting the compound of the formula (VII) with a halogenating reagent in an inert organic solvent at a temperature from −10° to 60° C.

Examples of the solvent to be used are benzene, toluene, carbon tetrachloride, dichloromethane, dichloroethane, chloroform, pyridine and ethyl ether.

Examples of the halogenating agents to be used are phosphorus trichloride, phosphorus tribromide, phosphorus oxychloride and preferably thionyl chloride.

The final step of this process can be carried out by heating, preferably at a temperature from 50° C. to 150° C., the compound of the formula (VIII) with the compound of the formula (IX) in the presence or absence of an organic solvent (e.g. benzene, toluene, xylene, methanol, ethanol, isopropyl alcohol).

It is particularly preferable to carry out the reaction in a sealed reaction vessel in the presence of sodium idodide.

When the 4-homoisotwistane derivatives of the formula (I-b) wherein both $R_3$ and $R_4$ are a hydrogen atom is desired, it is preferable to use potassium phthalimide as the compound (IX) since possible side-reaction may be avoided. In this case, the objective compound (I-b) can be obtained by treating the resultant product with hydrazine in a conventional manner.

Method C

The 4-homoisotwistane derivatives of the formula,

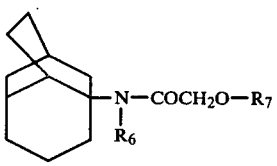

(I-c)

wherein $R_6$ is a $C_1$-$C_3$ alkyl group and $R_7$ is an alkyl group, an optionally substituted phenyl group or a group of the formula

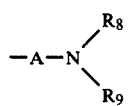

in which A is as defined above and

has the same meanings as

except the case where both $R_3$ and $R_4$ are hydrogen, and either $R_3$ or $R_4$ is hydrogen, can be prepared by reacting a compound of the formula,

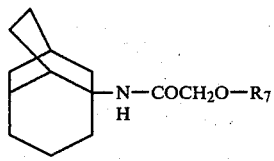

(I-d)

wherein $R_7$ is as defined above, with a reactive ester of a compound of the formula, $$R_6OH \qquad (X)$$

wherein $R_6$ is as defined above, in the presence of condensing reagents in an organic solvent at a temperature from room temperature (around 20° C.) to a boiling temperature of the used solvent.

Examples of condensing reagents to be used in the reaction are sodium hydride, sodium amide, sodium methoxide, potassium carbonate, sodium hydroxide, potassium hydroxide, and sodium carbonate.

Preferred reactive esters of the compound (X) are halide (e.g. chloride, bromide, iodide) aryl sulfonate (e.g. p-toluenesulfonate, benzenesulfonate) or alkyl sulfonate (e.g. methanesulfonate) thereof.

Examples of the solvents to be used in the reaction are benzene, toluene, xylene, dimethylacetamide, dimethylformamide, tetrahydrofuran, dioxane and dimethylsulfoxide.

In this reaction, the compound of the formula (I-d) may be used in the form of metal salt, which may be obtained by reacting the compound (I-d) with said condensing agents in a conventional way.

The 4-homoisotwistane derivatives of the formula (I) wherein $R_2$ is a group of the formula

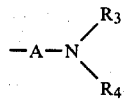

wherein A, $R_3$ and $R_4$ are as defined above except phthalimide, may be converted into the acid addition salt form by reacting them with organic or inorganic acids (e.g. hydrochloric acid, hydrobromic acid, sulfonic acid, p-toluenesulfonic acid, oxalic acid, citric acid, tartaric acid, lactic acid, phosphoric acid and the like).

The starting material of this invention, 3-amino-4-homoisotwistane is prepared by known method [i.e. Koji Aigami et al. J. of Medicinal chemistry 19, 536 (1976)].

In the following, the antiviral activities and effective dosages of the compounds (I) are described.

Ex. 1. Effects of the compounds (I) on the growth of herpes virus in tissue cultures Antiviral activities were determined by the tube dilution method. The cells used for the assay were KB cells.

KB cells were cultured in Eagle MEM medium. The medium was supplemented with 10% fetal calf serum.

The monolayer of cells grown in tube was exchanged to the fresh medium supplemented with 2% fetal calf serum, then 1000 TCD$_{50}$ of herpes simplex type I (HF strain) and the test compound were added.

After 72 hr. incubation at 37° C. virus induced cytopathic effect (CPE) and the cytotoxicity of the compound were determined by microscopic examination. Minimus virus growth inhibition concentration (MIC) and minimum cytotoxic concentration (MCC) were shown in Table I.

TABLE I

The effect of the compounds (I) on growth of Herpes simplex virus

| Compounds | Host cells | MIC (μg/ml) | MCC (μg/ml) |
|---|---|---|---|
| N-[3-(4-homoisotwistyl)]-2-(2-dimethylaminoethoxy) acetamide hydrochloride | KB | 50 | 250 |
| N-[3-(4-homoisotwistyl)]-2-ethoxy acetamide | KB | 10 | 25 |
| N-[3-(4-homoisotwistyl)]-2-pentyloxyacetamide | KB | 5 | 5 |
| N-[3-(4-homoisotwistyl)]-2-undecyloxyacetamide | KB | 2.5 | 10 |
| Amantadine hydrochloride | KB | 50 | >50 |

Ex. 2 Effects of the compounds (I) on experimental Influenza virus infection

The antiviral activities were determined by the modified Horsfall's method [Tani et al., Fukuoka Igaku Zasshi, 58, 9 (1967)].

Drug preparation

The compounds (I) and Amantadine hydrochloride as a control were dissolved in sterile physiological saline or suspended in 5% arabia gum saline solution for injection.

Animals ddY male mice weighing about 21 g were used in this study. Ten animals were used in each Experiment.

Virus

Influenza AoPR/8 was used.

Drug evaluation

Five LD$_{50}$ of influenza AoPR/8 was used for infecting mice by the aerosol. Subcutaneous drug treatment using various dosages started at 3 hours pre, 2, 6, 18, 30, 42, 54, 66, 78, 90, 102, 114, 126, 138 and 150 hours post infection in order to determine the efficacy of the compound (I) and Amantadine hydrochloride. Lung lesion score (LLS) was determined 7 days after infection by sacrificing the animals. When the mice had died within 7 days after infection, LLS determination was also carried out.

Results were as follows;

TABLE II

| Compounds | Dosage (mg/kg) | Lung Lesion Score |
|---|---|---|
| Control | 0 | 4.8 |
| N-[3-(4-homoisotwistyl)]-2-(2-dimethylaminoethoxy)acetamide hydrochloride | 15 | 4.33 |
| N-methyl-N-[3-(4-homoisotwistyl)]-2-(2-dimethylaminoethoxy)acetamide hydrochloride | 15 | 4.50 |
| N-[3-(4-homoisotwistyl)]-2-phenoxy acetamide | 15 | 4.35 |
| Amantadine hydrochloride | 10 | 4.3 |

The compounds of the present invention have low toxicity. They do not show any toxic symptoms, when over 300 mg/kg of the compounds are subcutaneously administered to a mouse.

The compounds of the present invention show potent antiviral activity in vivo as well as in vitro, and can be used for the treatment of human herpes viral diseases such as herpes keratities, herpesencephalitis and herpeslabialis, and human influenza infectious. For this purpose, they may be made up in pharmaceutical preparations such as ointments, eye lotion, injections, tablets and the like.

The compounds of the present invention can be administered orally or parenterally at a level that is in the range from about 5 mg to about 50 mg per kg of body weight per day. For the oral or parenteral administration, they are made up alone or together with a conventional pharmaceutical carrier or diluent to a conventional solid or liquid pharmaceutical preparation (e.g. powders, granules, tablets, capsules, suspensions, emulsions, ointment, solutions) using the conventional methods in the pharmaceutical field.

The following examples are given to illustrate the present invention more precisely out it is not intended to limit the present invention thereto.

EXAMPLE 1

(a) N-[3-(4-homoisotwistyl)]-2-bromo acetamide

To a solution of 4.1 g of 3-amino-4-homoisotwistane in 100 ml of benzene were added 2.5 g of bromoacetylbromide in 50 ml of benzene with stirring under cooling with ice and the mixture was refluxed for ten minutes and cooled. The precipitated product was collected by filtration and washed with 10 ml of benzene three times. The filtrate was concentrated to a residue, which was crystallized from a mixed solvent of benzene and n-hexane to give 3.3 g (Yield. 93.0%) of crystals, m.p. 122.5°–123.5° C.

IR $\nu$(nujol, cm$^{-1}$): 3310 (NH), 1645, 1555 (—NH-COCH$_2$Br)

(b) N-[3-(4-homoisotwistyl)]-2-(2-dimethylaminoethoxy)-acetamide hydrochloride

To a solution of sodium dimethylaminoethylate, obtained from 50 mg of sodium metal and 1 ml of dimethylaminoethanol, in 3 ml of toluene were added 430 mg of N-[3-(4-homoisotwistyl)]-2-bromoacetamide with stirring at room temperature. The mixture was refluxed for 2 hours, cooled and diluted with benzene. The organic solution was washed with water, dried (Na$_2$SO$_4$), concentrated and the resultant residue was chromatographed over silica gel to give 0.41 g (Yield. 92.7%) of liquid. To a solution of this product in ethyl ether was added hydrogen chloride ethyl ether solution to give 305 mg of white crystals, m.p. 120°–122° C. (hygroscopic).

| NMR $\delta$(CDCl$_3$, TMS): | |
|---|---|
| 7.03 ppm | (singlet, 1H, —NH—) |
| 3.85 | (singlet, 2H, —COCH$_2$O—) |
| 3.60 | (triplet, J = 5.5 Hz, 2H, —OCH$_2$CH$_2$N$\diagup\diagdown$ ) |
| 2.50 | (triplet, J = 5.5 Hz, 2H, —OCH$_2$CH$_2$N$\diagup\diagdown$ ) |
| 2.30 | (singlet, 6H, —N(CH$_3$)$_2$) |
| 0.9–2.3 | (multiplet, 17H, ring proton) |

The following compounds were obtained by substantially the same procedure as described above:

N-[3-(4-homoisotwistyl)]-2-ethoxyacetamide, liquid

| NMR $\delta$(CDCl$_3$, TMS): | |
|---|---|
| 6.35 ppm | (singlet, 1H, NH) |
| 3.76 | (singlet, 2H, —COCH$_2$O—) |
| 3.55 | (quartet, J = 7.0 Hz, 2H, —OCH$_2$CH$_3$) |
| 1.23 | (triplet, J = 7.0 Hz, 3H, OCH$_2$CH$_3$) |
| 0.9–2.2 | (multiplet, 17H, ring proton) |

N-[3-(4-homoisotwistyl)]-2-pentyloxyacetamide, liquid

| NMR $\delta$(CDCl$_3$, TMS): | |
|---|---|
| 6.45 ppm | (singlet, 1H, —NH—) |
| 3.80 | (singlet, 2H, —COCH$_2$O—) |
| 3.48 | (triplet, J = 6.0 Hz, 2H, —O—CH$_2$—) |
| 0.93 | (triplet, J = 6.0 Hz, 3H, —CH$_2$CH$_3$) |
| 0.7–2.4 | (multiplet, 23H, ring proton and —OCH$_2$CH$_2$CH$_2$CH$_2$CH$_3$) |

IR $\nu$(liquid, cm$^{-1}$): 3400 (NH), 1680, 1515 (—NH-COCH$_2$—) N-[3-(4-homoisotwistyl)]-2-undecyloxyacetamide liquid

| NMR $\delta$(CDCl$_3$, TMS): | |
|---|---|
| 6.45 ppm | (singlet, 1H, —NH—) |
| 3.80 | (singlet, 2H, —COCH$_2$O—) |
| 3.47 | (triplet, J = 6.5 Hz, 2H, —OCH$_2$—CH$_2$—) |
| 0.87 | (triplet, J = 6.0 Hz, 3H, —CH$_2$CH$_3$) |
| 0.6–2.2 | (multiplet, 35H, ring proton and other proton of undecyl group) |

N-[3-(4-homoisotwistyl)]-2-phenoxyacetamide
m.p. 84°–85.5° C. Yield, 94.6%

| NMR $\delta$(CDCl$_3$, TMS): | |
|---|---|
| 7.5–6.8 ppm | (multiplet, 5H, benzene ring proton) |
| 6.4 | (singlet, 1H, —NHCO—) |
| 4.4 | (singlet, 2H, —COCH$_2$O—) |
| 0.8–2.3 | (multiplet, 17H, ring proton) |

EXAMPLE 2

(a)
N-[3-(4-homoisotwistyl)]-2-(2-hydroxyethoxy)acetamide

Sodium metal, 140 mg was dissolved in 11.2 g of ethyleneglycol, to which were added 1.71 g of N-[3-(4-homoisotwistyl)]-2-bromoacetamide. The mixture was stirred at 150° C. for 3 hours.

After completion of the reaction, the excess ethyleneglycol was removed under reduced pressure.

The resultant residue was diluted with 55 ml of carbon tetrachloride, and 45 ml of water. The mixture was stirred, separated and the water layer was extracted with 20 ml of carbon tetrachloride.

The combined carbon tetrachloride solution was concentrated to give 2.0 g of residue, which crystallized from petroleum ether. The crystals were collected, washed with petroleum ether and dried to yield 1.47 g of white crystals having a melting point of 70°–72° C., Yield 92.1%.

(b)
N-[3-(4-homoisotwistyl)]-2-(2-chloroethoxy)acetamide

To a mixture of 535 mg of N-[3-(4-homoisotwistyl)]-2-(2-hydroxyethoxy)acetamide and 3 ml of chloroform were added dropwise 300 mg of thionyl chloride in 1 ml of chloroform with stirring over a period of 5 minutes at a temperature below 5° C. The mixture was stirred for one hour below 10° C., and for 15 hours at room temperature. After completion of the reaction, the mixture was cooled and made just weakly acid with 0.6 g of pyridine below 10° C. To this solution were added 15 ml of chloroform and 15 ml of water and the mixture was stirred and then separated. The chloroform layer was washed with water, dried ($Na_2SO_4$) and the solvent was removed to give 0.52 g of brown liquid, Yield 91%.

IR $\nu$(liquid cm$^{-1}$): 3390 (NH), 1675, 1520 (NHCOCH$_2$—)

| NMR $\delta$(CDCl$_3$, TMS): | |
|---|---|
| 6.56 ppm | (singlet, 1H, NH) |
| 3.9 | (singlet, 2H, —COCH$_2$O—) |
| 3.74 | (singlet, 4H, —OCH$_2$CH$_2$Cl) |
| 0.9–2.2 | (multiplet, 17H, ring proton) |

(c)
N-[3-(4-homoisotwistyl)]-2-(2-morpholinoethoxy)acetamide hydrochloride

A mixture of 230 mg of N-[3-(4-homoisotwistyl)]-2-(2-chloroethoxy) acetamide, 3 ml of toluene, 351 mg of morpholine and 12 mg of sodium iodide was refluxed for 24 hours. To the mixture were added 5 ml of toluene and the precipitated inorganic substance was collected by filtration, which was washed with toluene.

The solution was concentrated under reduced pressure to give a residue, which was dissolved in 20 ml of 2 N hydrochloric acid. The acidic solution was treated with active carbon and washed with petroleum ether.

The water layer was made basic with sodium hydroxide aqueous solution and the precipitated oily substance was extracted with petroleum ether. The extracts were dried over potassium hydroxide. Anhydrous hydrogen chloride gas was bubbled into the solution, and the precipitated crystals were collected by filtration to give 0.28 g of white crystals (very hygroscopic).

| NMR $\delta$(CDCl$_3$, TMS): | |
|---|---|
| 4.18 ppm | (singlet, 2H, —COCH$_2$O—) |
| 3.2–4.15 | (multiplet, 12H, methylene proton of 2-morpholinoethoxy group) |
| 0.9–2.2 | (multiplet, 17H, ring proton) |

Example 3
N-[3-(4-homoisotwistyl)]-2-(2-methylaminoethoxy)acetamide

A mixture of N-[3-(4-homoisotwistyl)]-2-(2-chloroethoxy) acetamide (230 mg), sodium iodide (12 mg) and 30% methylamine ethanol solution (4.2 g) was heated with stirring at a temperature from 60° to 70° C. for 24 hours in an autoclave. After completion of the reaction, ethanol and the excess methylamine were removed to give 0.3 g of yellow liquid. The liquid was dissolved in 20 ml of 2 N hydrochloric acid and the solution was treated with an active carbon and then washed with petroleum ether. The acid solution was made basic with sodium hydroxide solution under cooling. The basic solution was extracted with petroleum ether and the extracts were dried over potassium hydroxide to give, after removal of the solvent, 160 mg of yellow liquid.

| NMR $\delta$(CDCl$_3$, TMS): | |
|---|---|
| 3.85 ppm | (singlet, 2H, —COCH$_2$O—) |
| 3.60 | (triplet, J = 5.5 Hz, 2H —OCH$_2$CH$_2$N$\diagup\diagdown$ ) |
| 2.77 | (triplet, J = 5.5 Hz, 2H —OCH$_2$CH$_2$N$\diagup\diagdown$ ) |
| 2.45 | (singlet, 3H, $\diagdown$N—CH$_3$ $\diagup$ ) |

EXAMPLE 4

(a)
N-[3-(4-homoisotwistyl)]-2-(2-phthalimidoethoxy)acetamide

A mixture of 300 mg of N-[3-(4-homoisotwistyl)]-2-(2-chloroethoxy) acetamide, 200 mg of potassium phthalimidate and 3 g of dimethylformamide was refluxed for 3.5 hours. The precipitated inorganic substance was collected by filtration and washed with 2 ml of dimethylformamide. The filtrate was concentrated under reduced pressure to 2 ml of solution, which was poured into 30 ml of water. The mixture was extracted with ethyl acetate and the organic layer was separated, dried over sodium sulfate to yield after removal of the solvent, 460 mg of yellow liquid, which crystallized from a small amount of ethanol and water, 380 mg. m.p. 120.5°–126.5° C.

IR $\nu$(nujol, cm$^{-1}$): 3370 (NH), 1710

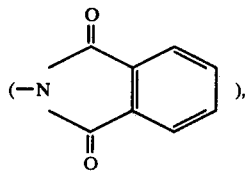

1675, 1530 (NHCO—)

(b) N-[3-(4-homoisotwistyl)]-2-(2-aminoethoxy) acetamide

A solution of 380 mg of N-[3-(4-homoisotwistyl)]-2-(2-phthalimidoethoxy) acetamide and 72 mg of 80% hydrazine hydrate in 2 ml of ethanol was refluxed for 4 hours. After cooling, 1.4 g of 10% hydrochloric acid were added to the mixture, which was stirred for 2 hours at a temperature from 60° to 70° C. and cooled. The precipitated crystals were collected by filtration and washed with a small amount of 10% hydrochloric acid.

The filtrate was made basic with sodium hydroxide and extracted with petroleum ether.

The extracts were dried over sodium sulfate to yield after removal of the solvent, 130 mg of liquid.

| NMR δ(CDCl₃, TMS): | |
| --- | --- |
| 7.75 ppm | (singlet, 1H, —NHCO—) |
| 6.67 | (singlet, 2H, —NH₂) |
| 3.85 | (singlet, 2H, —COCH₂O—) |
| 3.53 | (triplet, J = 5 Hz, 2H) |
| 3.64 | (triplet, J = 5Hz, 2H) |

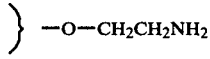

EXAMPLE 5

N-methyl, N-[3-(4-homoisotwistyl)]-2-(2-dimethylaminoethoxy) acetamide hydrochloride To a solution of 883 mg of N-[3-(4-homoisotwistyl)]-2-(2-dimethylaminoethoxy) acetamide in 10 ml of anhydrous dimethylformamide were added dropwise 166 mg of sodium hydride with stirring at room temperature. The mixture was stirred for 30 minutes at a temperature from 50° to 60° C. and cooled, to which a solution of 0.64 g of methyl iodide in 2 ml of anhydrous dimethylformamide was added dropwise. Then the mixture was stirred for one hour at room temperature and heated for 2 hours at 100° C. with stirring. The mixture was cooled and concentrated under reduced pressure to give a residue.

Water was added to the resulting residue and the mixture was extracted with chloroform and the chloroform layer was washed with water and dried. The solvent was removed under reduced pressure to give a yellow liquid, which chromatographd over silica gel to give 0.22 g liquid. The liquid was dissolved in ethyl ether, into which anhydrous hydrogen chloride gas was bubbled and the precipitated crystals were collected by filtration to give 140 mg of crystals, m.p. 169°–172.5° C. (hygroscopic)

| NMR δ(CDCl₃, TMS): | |
| --- | --- |
| 2.87 ppm | (singlet, 3H, —N—CO—)<br>   $\quad$   CH₃ |
| 2.3 | (singlet, 6H, —N(CH₃)₂) |

What is claimed is:

1. A compound of the formula,

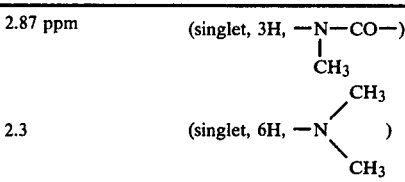

wherein R₁ is hydrogen; R₂ is C₁–C₁₁ alkyl, or non-toxic, pharmaceutically acceptable salts thereof.

2. N-[3-(4-homoisotwistyl)]-2-ethoxy acetamide.
3. N-[3-(4-homoisotwistyl)]-2-pentyloxyacetamide.
4. N-[3-(4-homoisotwistyl)]-2-undecyloxyacetamide.
5. A virucidal composition comprisng a virologically effective amount of a compound of claim 1 and a pharmaceutically acceptable carrier.
6. A method of treating virus infections which comprises administering a therapeutically effective amount of a composition of claim 5 to mammals.

* * * * *